United States Patent [19]

Gratacos et al.

[11] 4,111,040

[45] Sep. 5, 1978

[54] TESTING FOR CORROSION OF THE INTERNAL WALL OF A METAL CHAMBER

[75] Inventors: Jaime Gratacos, Morlaas; Christian Perrolet, Pau; Roger Mousteou, Billere, all of France

[73] Assignee: Societe Nationale Elf Aquitaine (Production), Paris, France

[21] Appl. No.: 819,045

[22] Filed: Jul. 26, 1977

[30] Foreign Application Priority Data

Jul. 30, 1976 [FR] France ................................ 76 23398

[51] Int. Cl.$^2$ ........................................... G01B 19/32
[52] U.S. Cl. ..................................................... 73/105
[58] Field of Search .................... 73/52, 49.5, 86, 105, 73/592, 627, 629, 630; 340/239 R, 239 F, 242, 243

[56] References Cited

U.S. PATENT DOCUMENTS

| 2,105,479 | 1/1938 | Hayes | 73/67.8 R |
|---|---|---|---|
| 3,020,760 | 2/1962 | Schnoll | 340/239 R X |
| 3,080,748 | 3/1963 | Burkley | 73/88.5 R |
| 3,603,142 | 9/1971 | Saylak et al. | 73/104 X |
| 3,721,898 | 3/1973 | Dragoumis et al. | 73/49.1 |
| 3,930,556 | 1/1976 | Kusuda et al. | 340/242 X |
| 3,995,472 | 12/1976 | Murray | 340/242 |

Primary Examiner—James J. Gill
Attorney, Agent, or Firm—Brisebois & Kruger

[57] ABSTRACT

Device for the detection of corrosion of the internal wall of a metal chamber. The device comprises at least one apparatus for measuring a physical quantity as a function of the condition of the surface of the internal wall of the chamber, such apparatus comprising a detection device having a detection surface and connected to an apparatus to measure and to calculate, and at least one means for transmitting these measurements, in which the detection surface of the detection device is applied to a surface element of the external wall of the chamber, the detection device being entirely covered by the casing isolating the chamber from the exterior environment. The device is particularly adapted for the inspection of and control of corrosion on the internal wall of conduits for transporting hydrocarbons which are buried in, or on, the sea floor.

10 Claims, 5 Drawing Figures

U.S. Patent    Sept. 5, 1978    4,111,040
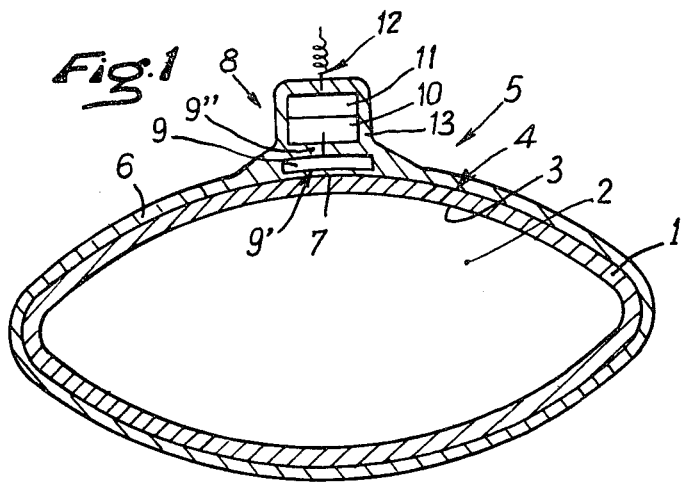
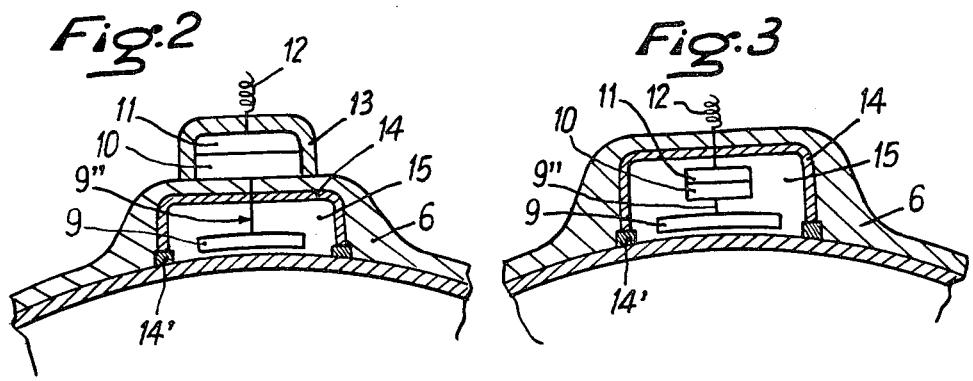
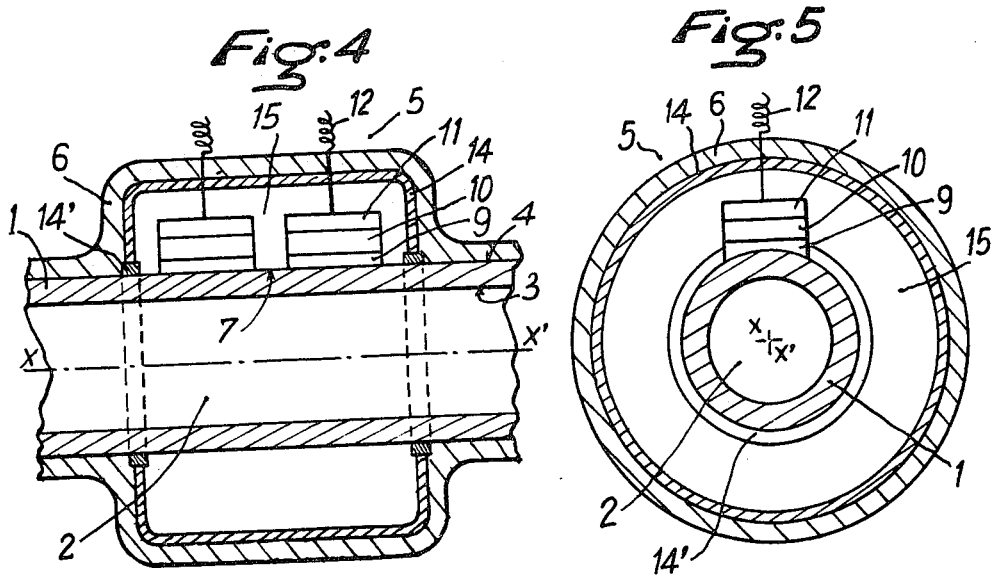

TESTING FOR CORROSION OF THE INTERNAL WALL OF A METAL CHAMBER

SUMMARY OF THE INVENTION

The present invention relates to an arrangement for detecting and thus controlling corrosion on the inside of a metal chamber, particularly undersea pipelines used for transferring or conveying liquid or gaseous hydrocarbons.

Several different methods are known for detecting such corrosion inside metal chambers installed on land, and therefor accessible, and particularly pipelines used on land for conveying liquid or gaseous hydrocarbons.

In these, or in different localizations, where the external wall of the chamber or the pipeline is covered by a casing protecting it from corrosion and from exterior erosions, the casing is removed to provide exposed zones where the detection surfaces of measuring devices are attached. The measurements are taken successively and discontinuously in different locations, assuring inspection for corrosion for all of the structure, localized metal chamber, or pipeline of great length.

The method of checking on the exposed zones of the chamber (or of the pipeline) in advance has been adopted on land taking into account the significant cost of apparatus for detection and for measurement and the eventual deterioration if these machines are left at the different locations between two series of measurements.

Such devices are useless in the sea: if the height of the sea is only a little high, the transportation of the apparatus and its manipulation present insurmountable difficulties.

The present invention overcomes these inconveniences by placing equipment for measurement and for detection directly on the chamber or pipeline in different detection zones protected from the exterior environment. The problems to be resolved being essentially those posed by the water-tightness of the installation, and the sturdiness and the viability of detection equipment permitting no maintenance work to be performed during the life of the installation.

The installation of equipment for detection and for measurement at locations determined in advance permits different tasks to be done, such as preparation of surfaces, placing of equipment, and calibration, particularly setting to zero, in the workshop, which results in a precision and a viability of measurements far superior to those obtained by successive and discontinuous measurements on land with transferable equipment.

A device for the detection of corrosion on the inside of a metal chamber containing a fluid which can be corrosive and separating said fluid from the exterior environment, the chamber whose external wall is encircled by a casing isolating the external wall from the exterior environment, comprises at least one measuring apparatus for measuring a physical quantity which is a function of or indicative of the condition of the internal surface of the chamber wall, such an apparatus comprising detection means connected to a mechanism for measuring and for calculating and at least one means for the transmission of the measurements. Such a device, according to the invention, has detection means which are applied on the external surface of the wall of the chamber, the means of detection being entirely covered by the casing isolating the chamber from the exterior environment.

The detection means comprise a detection device bounded particularly by a detection surface, the detection surface being applied on one surface element of the external wall of the chamber, the detection device being entirely covered by the wall or casing isolating the chamber from the exterior environment.

In accordance with a preferred embodiment, the element of the external wall of the chamber, on which the detection surface is applied, includes at least one measuring device, and the equipment is located in a non-corrosive region between a zone of the said external wall and a rigid plate in the form of a cover, itself covered exteriorly by the casing isolating the chamber from the exterior environment, the detection device being situated in the said non-corrosive region.

In the same embodiments, for each measuring apparatus, the detection device, the apparatus for measurement and for calculating, and the means of transmitting the measurements are generally situated in the non-corrosive region.

Such embodiments are particularly used when the chamber stores hydrocarbons.

When the chamber is a cylindrical pipeline, it is generally preferred that the rigid plate in the form of a cover be a section of a cylindrical pipe in the form of a sleeve encircling the chamber, with watertight annular seals or joints joining the extremities of said sleeve to the external wall of the chamber.

Such embodiments are used for cylindrical pipelines which transfer liquid or gaseous hydrocarbons and especially for such pipelines when they are submerged under a given depth of water.

The invention will be better understood in the description given as a non-limiting example, with the aid of the following drawings, of different embodiments of the device for checking the corrosion of the inside of a chamber containing a fluid which can be corrosive.

BRIEF DESCRIPTION OF THE DRAWINGS

FIG. 1 is a cross-sectional view of an arrangement in which the detection device is covered by a casing isolating the chamber from the exterior environment;

FIG. 2 is a partial sectional view of an arrangement in which the detection device is situated in a non-corrosive region isolated from the exterior environment by a plate in the form of a cover;

FIG. 3 is a partial sectional view of an arrangement in which the measuring apparatus is entirely situated in a non-corrosive region isolated from the exterior environment by a plate in the form of a cover;

FIG. 4 is a view in longitudinal section of a cylindrical pipeline, having a detecting device cover in the form of a cylindrical sleeve; and FIG. 5 is a transverse section of the arrangement of FIG. 4.

In FIG. 1, a chamber 1, for example of thick sheet metal such as steel, contains a fluid 2, at rest or moving, for example, by convection movements or flow, this fluid being totally or partially corrosive if it has heterogeneity.

Chamber 1 has a wall with an internal surface 3 which can be the region subject to corrosion by the fluid 2, and an external surface 4, separated and isolated from the outside environment 5 by a sheath or casing 6.

In a region 7 defined by a chamber is apparatus 8 for detecting corrosion comprising a detection device 9 having a detection surface 9' applied on the defined region 7. In region 7 the surface of chamber 1 can be prepared, as by machining so the thickness of the metal of the chamber 1 is constant within several thousandths of a millimeter throughout this region. The detecting apparatus 8 also comprises an apparatus 10 for measurement and for calculating and a means 11 for transmitting these measurements to which is connected a data transmission line 12. Instead of line 12 there can be a channel for Hertzian waves, adjacent a receiver, for recording and for interpreting the data from the detection apparatus.

In FIG. 1 the detection device 9 is connected by at least one conductor 9" to the apparatus for measuring and for calculating. Detection device 9 is enclosed by the same casing 6 which isolates chamber 1 from the exterior environment 5. Conductor 9" goes through casing 6 and the apparatus for measuring and for calculating and the transmission means are enclosed by their own casing 13, to isolate them from the exterior region 5.

In FIG. 2, the same elements are shown. Also, a plate 14 in the form of a cover is hermetically sealed to the external surface 4 of chamber 1 by a seam 14' so as to encircle zone 7. This plate can be metal or of a plastic material, and it isolates a space 15 containing a non-corrosive fluid. The detection device 9 is found in this space 15. Plate 14 is isolated from the exterior environment 5 by casing 6 which isolates the chamber 1 from said exterior environment. Chamber 13 contains the calculating and measuring apparatus.

In FIG. 3 we find the same elements as in FIG. 2, however, in space 15 are placed, not only the detection device 9 but also the apparatus for measuring and for calculating 10, and the transmission means 11.

FIG. 4 shows an arrangement where the chamber is a cylindrical tube or pipe with axis $xx'$ in which, for example, a liquid or gaseous hydrocarbon flows. Plate 14 takes the form of an annular sleeve 14 hermetically fastened to the external surface 4 of the pipe 1 by means of a seam 14' so as to surround zone 7 which is a section of the external surface 4.

On this zone 7 is applied at least one device for detection and for measurement of a physical quantity as a function of the area of the internal surface 3 of the pipe wall. Two such devices are shown, arranged in the annular space 15 bounded by the internal surface of sleeve 14 and by zone 7 of the external surface 4 of chamber 1.

Sleeve 14 is isolated from the exterior environment 5 by the same casing 6 which isolates the entire chamber 1, here cylindrical tube 1, from exterior environment 5.

Several types of detecting or inspection devices are currently used to detect the appearance and extent of corrosion on the inside of a receptacle such as a pipeline. They use eddy (Foucault) currents, ultrasonics, or gamma radiation.

The devices using ultrasonics or gamma radiation are used in mobile installations. The devices using the measurement of characteristics by eddy currents are used only in fixed installations since they comprise windings around the tube to be checked.

The installation at fixed positions of corrosion detectors, on a receptacle, permits the surfaces to be prepared in the workshop or mill at the precise location for the detectors. These devices can be installed and calibrated for zero corrosion in a laboratory of a workshop.

This technique, usable for pipelines placed on the ground and underground, can be applied also to pipelines installed on the sea floor.

While the actual techniques used above ground are not applicable to marine pipelines, the arrangements according to the present invention permit the checking or testing for the appearance of corrosion and the diminishing of this corrosion by application of anti-corrosion treatments. This control will assure, for underwater pipelines for the conveyance of hydrocarbons, a longevity suitable to the duration of exploitation of the production fields.

The detection devices of the types mentioned above are sensitive to variations in thickness of the wall, especially to the reduction of thickness due to corrosion, eventually aggravated by the effect of erosion caused by fluids in motion.

Independently or concurrently with the devices of the types mentioned above, a corrosion detecting apparatus 8 can be used comprising as detection device 9 at least one stress (or strain) gauge applied on a zone 7 of the external wall of the chamber 1 (in FIG. 1) or of the pipeline 1 (in FIG. 4).

The stress gauges are sensitive not only to variations in thickness of the mass of metal concerned, but also to the continuity of this metal. They permit detection of corrosion cracks, this corrosion characteristically fissuring is able to penetrate deeply into the metal without the thickness being aggregately affected. This form of corrosion is especially detrimental to the longevity of receptacles and metal pipelines. Due to stress gauges applied in a permanent fashion on fixed and protected detection surfaces, it is possible to detect this form of corrosion and thus to take steps to control it.

Where a data transmission line 12 is used, this transmission line can be extended to the next location where detection apparatus is located, to eventually form a cable of multiple lines 12 which can, for example, be accessible for connection to suitable receiving equipment, either portable or at fixed locations, such as tanker loading installations, and which can periodically monitor the various detection apparatuses. Alternatively, where the pipeline is buried on land, transmission line 12 can be extended to the surface of the earth for periodic monitoring by readily movable portable equipment which can be backpacked or carried in a suitable vehicle, such as an all terrain vehicle.

Where the means of transmission is a radio wave or perhaps sonar wave transmitter, the transmitter can transmit waves of a frequency or amplitude indicative of the extent of corrosion (if any) at the location of the detecting device on the pipeline.

Where the detection device is a strain gauge or stress gauge, it will readily be apparent that the resistance of devices forming such gauges can form part of an oscillator circuit of a transmitter, which periodically emits a signal, and the frequency of which is dependent on the resistance of its oscillator circuit. Since corrosion or cracks in the internal wall of the pipeline will either cause the external wall to expand if the pressure inside the pipe is greater, or to contract if the pressure outside the pipe is greater, a difference in the emitted frequency will serve as an indication of the existence of corrosion. The pre-calibrated detection apparatus, arranged according to the invention, provides sufficient accuracy so that even slight corrosion will cause its normal signal to deviate sufficiently to be detected by known equipment.

Variations and changes can of course be made without departing from the scope of this invention.

What is claimed is:

1. An arrangement for detecting corrosion of the internal wall of a metal pipeline containing a fluid which can be corrosive, the pipeline isolating the fluid from the exterior environment, a casing surrounding the external wall of the pipeline and isolating the wall from the external environment, the arrangement comprising a rigid cylindrical sleeve encircling the pipeline, annular watertight seams joining the ends of the sleeve to the outside wall of the pipeline, said sleeve defining a non-corrosive isolated region, said casing surrounding the external wall of the pipeline and said sleeve and isolating the wall and sleeve from the external environment, at least one measuring apparatus in said non-corrosive region of said sleeve for measuring a physical quantity indicative of the condition of the surface of the internal wall of the pipeline, said apparatus comprising means for detection and including a detection device having a detection surface applied to the external wall of the pipeline, means in said non-corrosive region for measuring and for calculating the output of the detection device, and means in the non-corrosive region for transmission of the measurements to a remote location.

2. A system for detecting corrosion of the internal surface of a wall of a metal chamber containing a corrosion fluid comprising, a plurality of individual, sealed, rigid enclosures at spaced apart locations on the outside of said chamber wall, means in each of said chambers for detecting a physical quantity indication of the condition of the internal surface of the chamber wall, means connected to said detecting means for measuring and calculating the quantity, means connected to said measuring means for transmitting the measurement to a remote location, and means covering said enclosures and the exterior of said chamber wall for isolating the wall and the chambers from the external environment.

3. A system according to claim 2 wherein said measuring means, and said transmitting means are each respectively within said enclosures.

4. A system according to claim 2, further comprising an addition enclosure associated with each aforementioned enclosure, each additional enclosure being sealed with respect to, and separate from its aforementioned enclosure, said measuring means and said transmitting means being mounted in said additional enclosures, and said means covering said enclosures covers said additional enclosures.

5. A system according to claim 2 wherein, said detecting means comprises a detecting device having a detecting surface engaging the external surface of the chamber wall.

6. Arrangement for the detection of corrosion, according to claim 5, in which the detection device having a detection surface includes at least one stress gauge.

7. Arrangement for detecting corrosion, according to claim 2, in which the chamber stores hydrocarbons.

8. Arrangement for detecting corrosion, according to claim 2, in which the chamber is a cylindrical pipeline.

9. Arrangement for detecting corrosion, according to claim 7, in which the cylindrical pipeline has hydrocarbons moving through it.

10. Arrangement for detecting corrosion, according to claim 9, in which the cylindrical pipeline is submerged to a given depth in water.

* * * * *